United States Patent
Higuchi et al.

(10) Patent No.: US 10,955,426 B2
(45) Date of Patent: Mar. 23, 2021

(54) METHOD FOR QUANTIFYING CHOLESTEROL IN HIGH-DENSITY LIPOPROTEIN 2, AND REAGENT KIT FOR THE METHOD

(71) Applicant: DENKA SEIKEN CO., LTD., Tokyo (JP)

(72) Inventors: Maiko Higuchi, Gosen (JP); Yasuki Itoh, Gosen (JP)

(73) Assignee: DENKA COMPANY LIMITED, Tokyo (JP)

( * ) Notice: Subject to any disclaimer, the term of this patent is extended or adjusted under 35 U.S.C. 154(b) by 0 days.

(21) Appl. No.: 16/019,175

(22) Filed: Jun. 26, 2018

(65) Prior Publication Data
US 2018/0306823 A1    Oct. 25, 2018

Related U.S. Application Data

(62) Division of application No. 14/001,766, filed as application No. PCT/JP2012/054797 on Feb. 27, 2012, now Pat. No. 10,031,145.

(30) Foreign Application Priority Data

Feb. 28, 2011 (JP) .............................. JP2011-042374

(51) Int. Cl.
*G01N 33/92* (2006.01)
*C12Q 1/60* (2006.01)

(52) U.S. Cl.
CPC .............. *G01N 33/92* (2013.01); *C12Q 1/60* (2013.01); *G01N 2333/916* (2013.01)

(58) Field of Classification Search
CPC ..... C12Q 1/60; G01N 33/92; G01N 2333/916
See application file for complete search history.

(56) References Cited

U.S. PATENT DOCUMENTS

| 2005/0095658 | A1 | 5/2005 | Matsui et al. | |
| 2009/0023167 | A1 | 1/2009 | Miyauchi et al. | |
| 2009/0170139 | A1* | 7/2009 | Mishima | C12Q 1/60 435/11 |
| 2009/0181413 | A1* | 7/2009 | Itoh | C12Q 1/60 435/11 |
| 2010/0255516 | A1 | 10/2010 | Itoh et al. | |
| 2013/0171674 | A1 | 7/2013 | Higuchi et al. | |

FOREIGN PATENT DOCUMENTS

| CN | 103080332 A | 5/2013 |
| EP | 0 698 791 A1 | 2/1996 |
| JP | 2001-346598 | 12/2001 |
| JP | 2009-207463 | 9/2009 |
| JP | 2009207463 A * | 9/2009 |

OTHER PUBLICATIONS

Caramelo et al. Mapping the catalytic pocket of phospholipases A2 and C using a novel set of phosphatidylcholines. Biochem J (2000), v346, p. 679-690. (Year: 2000).*
Dippe et al. Substrate specificity in phospholipid transformations by plant phospholipase D isoenzymes. Phytochemistry (2009), v70, p. 361-365. (Year: 2009).*
Perret et al. Distribution of high-density lipoprotein 2 and 3 constituents during in vitro phospholipid hydrolysis. 1987, Eur. J. Biochem., v279-286. (Year: 1987).*
Von Eckardstein et al. High Density Lipoproteins and Arteriosclerosis Role of Cholesterol Efflux and Reverse Cholesterol Transport. 2001, Arterioscler Thromb Vasc Biol., v21, p. 13-27. (Year: 2001).*
Ogino et al. Catalase catalyzes nitrotyrosine formation from sodium azide and hydrogen peroxide. Free Radical Research (2001), 35(6), 735-747. (Year: 2001).*
Teixeira et al. Determination of Catalase Activity and its Inhibition by a Simple Manometric Method. Biochemical Education (1992), 20(3), 174-175. (Year: 1992).*
Teixeria et al. Determination of Catalase Activity and its Inhibition by a Simple Manometric Method. Biochemical Education (1992), 20(3), 174-175. (Year: 1992).*
Chinese Office Action and Search Report, dated Mar. 31, 2015, for Chinese Application No. 201280020681.7.
Extended European Search Report, dated May 15, 2015, for European Application No. 12752957.6.
Hirano et al., "A simple and precise method for measuring HDL-cholesterol subfractions by a single precipitation followed by homogenous HDL-cholesterol assay", J. Lipid Res., vol. 49 (2008) pp. 1130-1136.
Ito et al., "Development of a Homogeneous Assay for Measurement of High-density Lipoprotein-subclass Cholesterol,"Clinica Chimica Acta, vol. 427, 2014, pp. 86-93.
Koga et al., "Measurement of HDL subfractions and its clinical significance", Rinsho Byori, vol. 31, No. 2 (1983) pp. 121-125.
Talameh et al., "Measurement of total HDL, HDL2, and HDL3 by dextran sulfate-MgCl2 precipitation technique in human serum", Clinica Chimica Acta, vol. 158 (1986) pp. 33-41.
"Centrifuge", Medical Discoveries, 1997, Retrieved Sep. 23, 2015 from Encyclopedia.com: http://www.encyclopedia.com/doc/1G2-3498100069.html.
Caramelo et al., (2000), "Mapping the catalytic pocket of phospholipases A2 and C using a novel set of phosphatidylcholines", Biochem J., v346, p. 679-690.

(Continued)

*Primary Examiner* — Sean C. Barron
(74) *Attorney, Agent, or Firm* — Birch, Stewart, Kolasch & Birch, LLP

(57) ABSTRACT

Disclosed is a method for quantifying HDL2 cholesterol in a test sample without requiring laborious operations. The method for quantifying cholesterol comprises allowing phospholipase to act on HDL to quantify cholesterol. Also disclosed is a method comprising: a first step of transferring cholesterols other than high-density lipoproteins in a test sample to the outside of the reaction system; and a second step of quantifying high-density lipoprotein 2 cholesterol among the high-density lipoproteins remaining in the reaction system; wherein, by performing the second step by the above method, high-density lipoprotein 2 cholesterol in the test sample can be quantified.

13 Claims, No Drawings

(56) References Cited

OTHER PUBLICATIONS

Dangerfield et al., (1976), "Serum lipoproteins and atherosclerosis in animals", Atherosclerosis, v25(1), p. 95-106.
Dippe et al., (2009), "Substrate specificity in phospholipid transformations by plant phospholipase D Isoenzymes", Phytochemistry, v70, p. 361-365.
Higuchi et al, (2011), "Development of a Novel Homogeneous Assay for Small HDL", Artherosclerosis Suppl., v12(1), p. 106.
Perret et al. (1987), "Distribution of high-density lipoprotein 2 and 3 constituents during in vitro phospholipid hydrolysis", Eur. J. Biochem, v279-286.
Phospholipids, (1999), In E. Hodgson et al. (Eds.) MacMillan Dictionary of toxicology, Basingstoke, United Kingdom: MacMillan Publishers Ltd. Retrieved from http://search.credoreference.com/content/entry/mactox/phospholipids/0.
Simard et al., (1989), "Phosphatidylcholine and Triacylglycerol hydrolysis in HDL as induced by hepatic lipase: modulation of the phospholipase activity by changes in the particle surface or in the lipid core", Biochmica et Biophysica Acta, v1001(2), p. 225-233.
Von Eckardstein et al., (2001), "High Density Lipoproteins and Arteriosclerosis Role of Cholesterol Efflux and Reverse Cholesterol Transport", Arterioscler Thromb Vasc Biol. v21, p. 13-27.

\* cited by examiner

METHOD FOR QUANTIFYING CHOLESTEROL IN HIGH-DENSITY LIPOPROTEIN 2, AND REAGENT KIT FOR THE METHOD

CROSS REFERENCE TO RELATED APPLICATIONS

This application is a Divisional of co-pending U.S. application Ser. No. 14/001,766 filed on Nov. 5, 2013, which is a National Stage of PCT/JP2012/054797 filed on Feb. 27, 2012, which claims priority to Japanese Patent Application No. 2011-042374 filed on Feb. 28, 2011. The entire contents of all of the above applications are hereby incorporated by reference.

TECHNICAL FIELD

The present invention relates to a method for quantifying cholesterol in high-density lipoprotein 2 (which may be hereinafter referred to as "HDL2") (cholesterol in HDL2 may be hereinafter referred to as "HDL2 cholesterol"), and a reagent kit therefor.

BACKGROUND ART

Since high-density lipoprotein (HDL) receives cholesterol from various tissues including walls of blood vessels with arteriosclerosis, it is involved in the action of efflux of cholesterol accumulated in cells. Therefore, HDL cholesterol is also called the reverse cholesterol transport system. High-density lipoprotein is known to have negative correlation with arteriosclerotic diseases such as coronary arteriosclerosis. Accordingly, an HDL value lower than a predetermined lower limit is regarded as an indication of hyperlipidemia, and the value is known to be useful as an index of arteriosclerosis.

HDL is constituted by apoprotein, phospholipid, cholesterol and neutral fat. HDL has a density of $d=1.063$ to $1.210$ g/mL, and can be divided into two fractions, that is, HDL2, wherein $d=1.063$ to $1.125$ g/mL, and HDL3, wherein $d=1.125$ to $1.210$ g/mL. A notch is found at the portion of $d=1.125$ g/mL in the distribution curve of lipoprotein, and the part having higher densities in the curve corresponds to HDL3. Alternatively, HDL can be divided into subfractions based on the content of apolipoprotein E among the apoproteins in HDL, and HDLs having higher contents of apoE are defined as apoE-rich HDLs.

Conventionally, HDL is known to function not only as a whole but also as the individual HDL2 and HDL3 subfractions having different functions. HDL2 is known to have an antiatherogenic action. It is clinically known that CETP deficiency prevents metabolism of HDL to LDL or IDL, leading to an increase in the HDL cholesterol level. It is also said that the HDL increased by CETP deficiency is HDL2. Further, it is also said that CETP deficiency causes an increase in apoE-rich HDL, and that, since Apo-E-rich HDL has a strong cholesterol-efflux ability and antiplatelet action, it is a better HDL among HDLs. Further, a decrease in the hepatic lipase activity prevents conversion of HDL3 to HDL2, resulting in an increase in HDL3. That is, the ratios of subfractions of HDL may vary depending on the clinical condition, and measurement of HDL alone hardly allows detection of such changes. In view of such tendencies, it is expected that measurement of each of the HDL subfractions may contribute to judgment of whether or not a patient is suffering from a disease such as arteriosclerosis or hyperlipidemia, and of the cause of the disease. Further, at present, in view of these functions of HDL subfractions, manufacturers are developing therapeutic agents that inhibit the function of CETP, decrease the LDL cholesterol level, and increase the HDL cholesterol level.

Establishment of a simple method for measuring the HDL subfractions may lead to detailed elucidation of their functions, and to their therapeutic effects in the future.

Examples of the methods for measuring HDL subfractions that are known at present include ultracentrifugation, high-performance liquid chromatography (HPLC), HDL3 precipitation (Patent Document 1) and NMR.

In ultracentrifugation, fractionation is carried out utilizing the difference in the density of lipoprotein. This method has drawbacks in that the operation requires a skill; the method takes many days; and the cost is high. In the method by Okazaki et al. wherein HPLC is used for separating HDL2 and HDL3, the operation takes a long time, and special equipment is required. HDL3 precipitation is a method wherein a reagent containing a divalent metal ion and dextran sulfate is used to aggregate lipoproteins other than HDL3, and HDL3 in the supernatant portion is recovered by centrifugation and measured using an automatic analyzer. This method is not widely used since the method has drawbacks in that the operation of this method also requires a skill; the method is a manual method; the method requires an operation of sample pretreatment; and a certain length of time is required before measurement. Further, NMR, which is a method wherein the number of particles of lipoprotein is measured by nuclear magnetic resonance, is not commonly employed since the method requires special equipment.

There is a method for analyzing HDL subfractions (Patent Document 2). Although this method enables measurement with a general purpose automatic apparatus, the method employs a method wherein a surfactant is used to prevent an enzyme from acting on lipoproteins other than HDL3. By measuring HDL3 and subtracting the value of HDL3 from total HDL, HDL2 can be measured, but the method does not directly measure HDL2.

Thus, as an alternative to the above methods, a reagent that enables simple and more selective quantification of cholesterol in HDL2 needs to be invented.

PRIOR ART DOCUMENTS

Patent Documents

[Patent Document 1] JP 2009-207463 A
[Patent Document 2] JP 2001-346598 A

SUMMARY OF THE INVENTION

An object of the present invention is to provide a method for quantifying HDL2 cholesterol in a test sample without requiring laborious operations.

Problems to be Solved by the Invention

An object of the present invention is to provide a method for quantifying HDL2 cholesterol in a test sample without requiring laborious operations. Another object of the present invention is to provide a reagent kit for quantification of HDL2 using the method of the present invention.

Means for Solving the Problems

As a result of intensive study, the present inventors found conditions where phospholipase acts on HDL2 but hardly acts on HDL3 among HDLs, and discovered a method in which HDL2 can be preferentially measured by utilizing phospholipase. This was then experimentally confirmed to be realizable, to complete the present invention.

That is, the present invention provides a method for quantifying cholesterol of HDL2, which method comprises allowing phospholipase to act on HDL and quantifying cholesterol. Further, the present invention provides a kit for quantifying cholesterol in high-density lipoprotein 2 by the above method of the present invention, which kit comprises phospholipase. Further, the present invention provides a method for quantifying high-density lipoprotein 2 cholesterol in a test sample, which method comprises: a first step of transferring cholesterols other than high-density lipoproteins in a test sample to the outside of the reaction system; and a second step of quantifying high-density lipoprotein 2 cholesterol among the high-density lipoproteins remaining in the reaction system; wherein the second step is carried out by the above method of the present invention.

Effect of the Invention

By the present invention, HDL2 cholesterol in a test sample can be specifically quantified with an automatic analyzer without requirement of laborious operations such as ultracentrifugation or pretreatment. Further, quantification of the HDL3 cholesterol level can also be carried out by subtracting the HDL2 cholesterol level from the total HDL cholesterol level obtained by a conventional method for quantifying the total HDL cholesterol in a test sample.

BEST MODE FOR CARRYING OUT THE INVENTION

As described above, the method for quantifying HDL2 cholesterol of the present invention comprises allowing phospholipase to act on HDL and then quantifying cholesterol. By applying this quantification method to a sample prepared by separating a test sample from a living body and then preliminarily removing cholesterol in lipoproteins other than HDLs therefrom, HDL2 cholesterol in the test sample can be quantified. That is, HDL2 cholesterol in a test sample can be quantified by application of the above-described method of the present invention as the second step of a method for quantifying HDL2 cholesterol in a test sample, which method for quantifying HDL2 cholesterol comprises: a first step of transferring cholesterols other than HDLs in a test sample to the outside of the reaction system; and a second step of quantifying HDL 2 cholesterol among the HDLs remaining in the reaction system. This two-step method is described below. It should be noted that, although the two-step method is described below, the second step of this two-step method is the method of the present invention (however, the two-step method itself is also the method of the present invention). Further, the first step described below is not necessarily required for carrying out the method of the present invention, and HDL2 cholesterol in a test sample can also be quantified by separating a test sample from a living body and removing only HDLs therefrom by another known method such as ultracentrifugation, followed by application of the method of the present invention to the HDLs (the second step described below). However, in this case, cholesterol oxidase and cholesterol esterase, which are required for quantification of cholesterol, need to be further supplied (in the two-step method described below, the cholesterol oxidase and cholesterol esterase used in the first step can be continuously used in the second step).

The test sample to be subjected to the method of the present invention is not limited as long as HDL2 cholesterol in the sample is to be quantified. The sample is preferably serum or blood plasma, or a dilution thereof. Serum or a dilution thereof is especially preferred.

The HDL2 to be measured by the present invention corresponds to larger HDL particles among the HDLs, such as the portion having densities of d=1.063 to 1.125 g/mL or particle sizes of 12.1 to 16 nm. However, these definitions are merely distinctions among HDLs, which have a continuous distribution, and the above-described values do not clearly limit the clinical significance. Since some general reports also use different distinctions in terms of the density, the HDLs in the large-particle side roughly within the above-described range are regarded as HDL2. In the large-particle side, apoE-rich HDLs and the like are also included in the range of measurement of the present invention.

In the first step of the present invention, a cholesterol-reactive enzyme(s) such as cholesterol esterase, cholesterol oxidase and/or cholesterol dehydrogenase, in addition to phospholipase, lipoprotein lipase and/or the like are added to the test sample to allow the reaction to proceed. Each of the phospholipase and lipoprotein lipase may be added either as a single enzyme or as a mixture of 2 or more types of the enzyme. In addition, a surfactant(s) may be used in the first step, and the above-mentioned enzymes and the surfactant(s) may be used in combination.

In the first step of the method of the present invention, cholesterol of the lipoproteins other than HDLs are transferred to the outside of the reaction system by the action of cholesterol esterase and/or the like. The term "transferred to the outside of the reaction system" herein means that cholesterol and esters thereof are eliminated or protected such that the cholesterol and esters thereof are not involved in the later steps.

The term "eliminate" herein means that cholesterol of lipoprotein in the test sample is degraded such that the cholesterol does not act on the reaction for measurement of cholesterol in a later step. Examples of the method for eliminating lipoprotein cholesterol include a method wherein cholesterol esterase and cholesterol oxidase are allowed to act on the cholesterol, followed by dissociation of the produced hydrogen peroxide into water and oxygen using catalase. Alternatively, a hydrogen donor may be reacted with the produced hydrogen peroxide using peroxidase to cause conversion to a colorless quinone. The method for eliminating lipoprotein cholesterol is not limited to these. The method of eliminating cholesterol per se is well-known in the art.

The term "protection" means to protect lipoprotein in the test sample such that the lipoprotein does not react upon cholesterol measurement in a later step. Examples of the method of protection of lipoprotein include, but are not limited to, a method wherein a surfactant is used to specifically protect each lipoprotein such that cholesterol esterase and cholesterol oxidase do not act on the lipoprotein.

In the first step, by preliminarily adding, individually or at the same time, an enzyme system and a surfactant for transferring the cholesterol to the outside of the reaction system, both steps can be carried out at the same time as a single step.

In the first step, in cases where cholesterol esterase and cholesterol oxidase are used, the concentration (the concentration means the final concentration unless otherwise specified in the present specification) of cholesterol esterase is preferably about 0.1 to 10.0 U/mL, more preferably about 0.2 to 2.0 U/mL. The concentration of cholesterol oxidase is preferably about 0.05 to 10.0 U/mL, more preferably about 0.1 to 1.0 U/mL. The cholesterol esterase is not restricted as long as it acts on ester-type cholesterol, and examples of the cholesterol esterase which may be used include commercially available products such as cholesterol esterase (CEBP, CEN) manufactured by Asahi Kasei Corporation, cholesterol esterase (COE-311, COE-313) manufactured by Toyobo Co., Ltd., and cholesterol esterase (CHE-XE) manufactured by Kikkoman Co., Ltd. The cholesterol oxidase is not restricted as long as it acts on free cholesterol, and examples of the cholesterol oxidase which may be used include commercially available products such as cholesterol oxidase (CONII) manufactured by Asahi Kasei Corporation, cholesterol oxidase (COO-311, COO-321, COO-331) manufactured by Toyobo Co., Ltd., and cholesterol oxidase (CHO-CE, CHO-PEWL, CHO-BS) manufactured by Kikkoman Co., Ltd.

In cases where cholesterol dehydrogenase is used, it is used at a concentration of preferably 0.01 to 200 U/mL, more preferably 0.1 to 100 U/mL. The cholesterol dehydrogenase is not restricted as long as it is an enzyme having an ability to oxidize cholesterol and to reduce an oxidized coenzyme. Examples of the cholesterol dehydrogenase that may be used include commercially available products such as cholesterol dehydrogenase (CHDH-5) manufactured by Amano Enzyme Inc.

Phospholipase and/or lipoprotein lipase may be further added, and, in such a case, the enzyme is used at a concentration of preferably about 0.01 to 0.5 U/mL, more preferably 0.02 to 0.5 U/mL. Examples of the lipoprotein lipase or phospholipase that may be used include commercially available products such as lipoprotein lipase (LPL-311 and LPL-314) manufactured by Toyobo Co., Ltd., lipoprotein lipase (LPL-3 and the like) manufactured by Amano Enzyme Inc., and lipoprotein lipase (LPBP, LP and the like) manufactured by Asahi Kasei Corporation. Examples of the phospholipase that may be used include sphingomyelinase (SPC), and phospholipase A2 (PLA2L), phospholipase D (PLD or PLDP or PLDPV) and phospholipase C (PLC), which are phospholipases, manufactured by Asahi Kasei Corporation. However, in cases where sphingomyelinase is used, the final concentration of sphingomyelinase is preferably about 0.05 to 50 U/mL, more preferably 0.1 to 30 U/mL. The sphingomyelinase is not limited as long as it acts on sphingomyelin, and may also have activities on components constituting phospholipids other than sphingomyelin, such as phosphatidyl inositol. Since phospholipase has only a small influence on HDL2 but can act on lipoproteins other than HDLs under the conditions in the first step including the phospholipase concentration, it allows easy transfer of lipoproteins other than HDLs to the outside of the reaction system.

In cases where a surfactant is added, it is added at a concentration of preferably 0.001 to 5.0% by weight, more preferably 0.002 to 3.0% by weight. Examples of the surfactant include, but are not limited to, anionic surfactants such as polyoxyethylene alkyl ether sodium sulfate; and nonionic surfactants such as polyoxyethylene-polyoxypropylene condensates, amide nonions, polyoxyethylene nonylphenyl ether, and polyoxyethylene polycyclic phenyl ether having an HLB value of 14 to 17. Specific examples of the surfactant include Pluronic P123 (ADEKA), Pluronic F68 (ADEKA), Pluronic F88 (ADEKA), Levenol WX (Kao Corporation), Nonion HS220 (NOF Corporation), Nymid MT-215 (NOF Corporation), Newcol-723 (Nippon Nyukazai Co., Ltd.), Newcol-2614 (Nippon Nyukazai Co., Ltd.) and Newcol-714 (Nippon Nyukazai Co., Ltd.).

As the reaction liquid to be used in the first step, various buffers used in normal biochemical reactions may be used, and the pH is preferably 5 to 8. The solution is preferably Good's, Tris, phosphate or glycine buffer solution, and is preferably a Good's buffer bis(2-hydroxyethyl)iminotris(hydroxyethyl)methane (Bis-Tris), piperazine-1,4-bis(2-ethanesulfonic acid) (PIPES), piperazine-1,4-bis(2-ethanesulfonic acid) 1.5 sodium salt monohydrate (PIPES 1.5Na), 2-hydroxy-3-morpholinopropanesulfonic acid (MOPSO), N,N-bis(2-hydroxyethyl)-2-aminoethanesulfonic acid (BES), 2-[4-(2-hydroxyethyl)-1-piperazinyl]ethanesulfonic acid (HEPES) or piperazine-1,4-bis(2-hydroxy-3-propanesulfonic acid) (POPSO).

In the first step, a monovalent and/or divalent cation(s) and/or a salt(s) thereof may be added in order to easily distinguish the lipoproteins other than HDLs. Specific examples thereof that may be used include sodium chloride, potassium chloride, manganese chloride, calcium chloride, ammonium chloride, magnesium sulfate, potassium sulfate, lithium sulfate, ammonium sulfate and magnesium acetate. The concentration is preferably 1 to 50.0 g/L, more preferably 5 to 30 g/L.

The reaction temperature in the first step is preferably about 25 to 40° C., more preferably 35 to 38° C., most preferably 37° C. The reaction time is not restricted, and is usually about 2 to 10 minutes.

Although the first step may be carried out in the absence of a surfactant, an enzyme such as sphingomyelinase may be used in combination with a surfactant.

Also in cases where the first step is carried out in the presence of a surfactant, the reaction conditions (reaction temperature, time, buffer and the like) are as described above.

In the subsequent second step, cholesterol in HDL2 among the HDLs remaining in the reaction system is quantified. This is carried out by allowing phospholipase to act on the HDLs remaining in the reaction system to preferentially measure the cholesterol in HDL2.

The phospholipase used in the second step acts on at least glycerophospholipid, and further preferably has activity on phosphatidyl choline. The phospholipase may also have activity on lysophospha ethanolamine and the like other than phosphatidyl choline, and/or sphingomyelin, ceramide and the like other than glycerophospholipids. As the phospholipase, a commercially available product may be used, and specific examples of the phospholipase that may be used include phospholipase A2 (PLA2L), phospholipase C (PLC), phospholipase D (PLD or PLDP or PLDPV) and lysophospholipase (LYPL) manufactured by Asahi Kasei Corporation. Phospholipase C and phospholipase D are especially preferred.

In cases where phospholipase is used in the second step, either a single type or a combination of a plurality of types of phospholipase may be allowed to act in the step. The concentration of phospholipase (final concentration, in cases where two or more types of phospholipase are used in combination) is preferably 0.5 to 200 U/mL, more preferably 1.0 to 100 U/mL, still more preferably 3.0 to 50 U/mL. In cases where phospholipase is used in the first step, the concentration of phospholipase used in the second step is higher than that in the first step.

In the second step, cholesterol is quantified utilizing the action of phospholipase and/or the like. Methods of quantification itself of cholesterol are well known, and any of the well known methods may be used. A specific description is also given in the Examples below. For example, ester-type cholesterol in lipoprotein is hydrolyzed with cholesterol esterase to produce free cholesterol and a fatty acid, and the produced free cholesterol and free cholesterol inherently existing in the lipoprotein are converted using cholesterol oxidase to generate cholestenone and hydrogen peroxide. A quinone pigment is then formed in the presence of peroxidase, and quantified. Examples of the compounds that generate a quinone pigment include HDAOS (N-(2-hydroxy-3-sulfopropyl)-3,5-dimethoxyaniline), DAOS (N-ethyl-N-(2-hydroxy-3-sulfopropyl)-3,5-dimethoxyaniline) or TOOS (N-ethyl-N-(2-hydroxy-3-sulfopropyl)-3-methylaniline) and 4-aminoantipyrine, but the compound is not restricted as long as the combination allows generation of a quinone pigment. In cases where cholesterol esterase and cholesterol oxidase are used in the first step, the cholesterol esterase and cholesterol oxidase used in the first step may be used as they are in the second step, without further addition thereof.

In cases where cholesterol esterase and cholesterol oxidase are used as enzymes reactive with cholesterol for measuring cholesterol, the enzymatic reaction generates hydrogen peroxide. By measuring the absorbance, at a wavelength of 400 to 700 nm, of the pigment formed from the generated hydrogen peroxide by coupling reaction between a hydrogen donor and a hydrogen receptor in the presence of peroxidase, cholesterol in HDL2 can be quantified.

In cases where cholesterol esterase and cholesterol dehydrogenase are used as enzymes reactive with cholesterol for measuring cholesterol, the enzymatic reaction generates NAD(P)H from NAD(P). By measuring the absorbance of the generated NAD(P)H at a wavelength of 330 to 400 nm, cholesterol in HDL2 can be quantified.

The concentration of the compound for generation of a quinone pigment is preferably about 0.5 to 2.0 mmol/L in the case of HDAOS, or 0.1 to 2.0 mmol/L in the case of 4-aminoantipyrine. The concentration of peroxidase is preferably 0.4 to 5.0 U/mL. In the process wherein hydrogen peroxide produced in the first step is decomposed using catalase, a catalase inhibitor sodium azide is used in the second step by inclusion in the reaction liquid. The concentration of sodium azide in this case is usually about 0.1 g/L to 1.0 g/L.

In cases where peroxidase is used in the first step, the concentration of peroxidase is preferably about 2.0 to 5.0 U/mL, more preferably about 3.0 to 4.0 U/mL. In cases where a compound that is converted to colorless quinone is used, the concentration of the compound is preferably about 0.4 to 0.8 mmol/L.

The second step does not necessarily require the presence of a surfactant, and a surfactant may be either added or not added. In cases where a surfactant is added, a surfactant that can be used in the first step is added at a concentration which is the same as, or lower than, the concentration in the first step.

The other reaction conditions for the second step (reaction temperature, time, buffer, pH and the like) may be the same as the reaction conditions for the first step described above.

The above-described methods for measuring HDL2 cholesterol by the first step and the second step may be combined to provide a reagent kit comprising the reagents described above.

Further, it is also possible to determine the HDL3 cholesterol level in the test sample by subtracting the HDL2 cholesterol level obtained by the first step and the second step, from the HDL cholesterol level in the test sample. Since the method for determining the HDL cholesterol level in a test sample is well known (for example, JP 2001-103998 A), and kits for the method are commercially available, the HDL cholesterol level can be easily quantified using these.

The present invention will now be described more concretely by way of Examples below. However, the present invention is not limited to the Examples below.

Example 1

HDL2 and HDL3 were recovered by ultracentrifugation, and Formulated Reagent A described below as the first step and Formulated Reagent I as the second step were used in combination to allow the reaction to proceed, to see whether the reaction occurs more specifically to HDL2 than HDL3 by use of phospholipase D in the second step. That is, more specifically, this method was carried out as follows. Ultracentrifugation is a method to prepare the fractions of CM, LDL, HDL2, HDL3 and the like based on the difference in the density of lipoprotein in a test sample such as serum, using a sodium bromide solution or the like. In the Examples of the present patent, the HDL2 fraction is a fraction comprising lipoproteins having densities of d=1.063 to 1.125 g/mL, and the HDL3 fraction is a fraction comprising lipoproteins having densities of d=1.125 to 1.210 g/mL. In the measurement, 150 μL of the formulated reagent for the first step is mixed with 2 μL of the ultracentrifugation fraction, and the reaction was allowed to proceed at 37° C. for 5 minutes, followed by mixing 50 μL of the formulated reagent for the second step therewith and allowing the reaction to proceed at 37° C. for 5 minutes. In terms of the wavelengths, a primary wavelength of 600 nm and a secondary wavelength of 700 nm were used.

By dividing the measured absorbance for HDL2 by the absorbance for HDL3, the ratio of reactivity between HDL2 and HDL3 was calculated, and the ratio was compared to that in a case where an HDL reagent was used in the test. The results are shown in Table 1. As the HDL reagent, HDL-EX, manufactured by Denka Seiken Co., Ltd., was used in the present Example.

| Formulated Reagent A | | |
|---|---|---|
| BES buffer | 100 mmol/L | pH 6.6 |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Pluronic F68 | 0.2 g/L | |
| Formulated Reagent I | | |
| BES buffer | 100 mmol/L | pH 7.0 |
| Sodium azide | 0.1% | |
| 4-Aminoantipyrine | 4.0 mmol/L | |
| Peroxidase | 2.4 U/mL | |
| Phospholipase D (PLDP) | 1.0 U/mL | |

TABLE 1

| Sample | Absorbance (mAbs) | | Ratio |
| --- | --- | --- | --- |
| | HDL2 | HDL3 | HDL2/HDL3 |
| HDL reagent | 60.5 | 60.0 | 1.0 |
| Formulated Reagent A, Formulated Reagent I | 55.2 | 7.0 | 7.9 |

The ratio observed with the formulated reagents was higher than that observed with the HDL reagent, and the results indicate that use of phospholipase D allows more preferential measurement of HDL2 than use of the HDL reagent.

Example 2

In the same manner as in Example 1, HDL2 and HDL3 were recovered by ultracentrifugation, and Formulated Reagent B or C described below as the first step and Formulated Reagent I as the second step were used in combination to allow the reaction to proceed. By dividing the measured absorbance for HDL2 by the measured absorbance for HDL3, the ratio of reactivity between HDL2 and HDL3 was calculated, and the obtained ratio was compared to that in a case where an HDL reagent was used in the test. The results are shown in Table 2. As the HDL reagent, HDL-EX, manufactured by Denka Seiken Co., Ltd., was used in the present Example.

| Formulated Reagent B | |
| --- | --- |
| BES buffer | 100 mmol/L pH 6.6 |
| HDAOS | 0.7 mmol/L |
| Catalase | 600 U/mL |
| Sodium chloride | 1 g/L |
| Cholesterol esterase | 1.4 U/mL |
| Cholesterol oxidase | 0.8 U/mL |
| Pluronic F68 | 0.25 g/L |
| Sphingomyelinase | 0.5 U/mL |

| Formulated Reagent C | |
| --- | --- |
| BES buffer | 100 mmol/L pH 6.6 |
| HDAOS | 0.7 mmol/L |
| Catalase | 600 U/mL |
| Sodium chloride | 1 g/L |
| Cholesterol esterase | 1.4 U/mL |
| Cholesterol oxidase | 0.8 U/mL |
| Pluronic F68 | 0.25 g/L |
| Sphingomyelinase | 1.0 U/mL |

| Formulated Reagent I | |
| --- | --- |
| BES buffer | 100 mmol/L pH 7.0 |
| Sodium azide | 0.1% |
| 4-Aminoantipyrine | 4.0 mmol/L |
| Peroxidase | 2.4 U/mL |
| Phospholipase D (PLDP) | 1.0 U/mL |

TABLE 2

| Sample | Absorbance (mAbs) | | Ratio |
| --- | --- | --- | --- |
| | HDL2 | HDL3 | HDL2/HDL3 |
| HDL reagent | 60.5 | 60.0 | 1.0 |
| Formulated Reagent B, Formulated Reagent I | 62.5 | 8.2 | 7.6 |
| Formulated Reagent C, Formulated Reagent I | 63.1 | 8.4 | 7.5 |

The ratios observed with the formulated reagents were higher than the ratio observed with the HDL reagent, and the results indicate that use of sphingomyelinase in the first step, followed by use of phospholipase D in the second step, allows more preferential measurement of HDL2 than use of the HDL reagent.

Example 3

In the same manner as in Example 1, HDL2 and HDL3 were recovered by ultracentrifugation, and Formulated Reagent D, E or F described below as the first step and Formulated Reagent I as the second step were used in combination to allow the reaction to proceed, to see whether the reaction occurs more specifically to HDL2 than HDL3 by use of phospholipase D in the first step at a lower concentration than in the second step, followed by use of phospholipase D also in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 3. As the HDL reagent, HDL-EX, manufactured by Denka Seiken Co., Ltd., was used in the present Example.

| Formulated Reagent D | |
| --- | --- |
| BES buffer | 100 mmol/L pH 6.6 |
| HDAOS | 0.7 mmol/L |
| Catalase | 600 U/mL |
| Sodium chloride | 1 g/L |
| Cholesterol esterase | 1.4 U/mL |
| Cholesterol oxidase | 0.8 U/mL |
| Pluronic F68 | 0.25 g/L |
| Phospholipase D (PLDP) | 0.1 U/mL |

| Formulated Reagent E | |
| --- | --- |
| BES buffer | 100 mmol/L pH 6.6 |
| HDAOS | 0.7 mmol/L |
| Catalase | 600 U/mL |
| Sodium chloride | 1 g/L |
| Cholesterol esterase | 1.4 U/mL |
| Cholesterol oxidase | 0.8 U/mL |
| Pluronic F68 | 0.25 g/L |
| Phospholipase D (PLDP) | 0.3 U/mL |

-continued

| Formulated Reagent F | | |
|---|---|---|
| BES buffer | 100 mmol/L pH 6.6 | |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Pluronic F68 | 0.25 g/L | |
| Phospholipase D (PLDP) | 0.5 U/mL | |

| Formulated Reagent I | | |
|---|---|---|
| BES buffer | 100 mmol/L pH 7.0 | |
| Sodium azide | 0.1% | |
| 4-Aminoantipyrine | 4.0 mmol/L | |
| Peroxidase | 2.4 U/mL | |
| Phospholipase D (PLDP) | 1.0 U/mL | |

TABLE 3

| Sample | Absorbance (mAbs) HDL2 | Absorbance (mAbs) HDL3 | Ratio HDL2/HDL3 |
|---|---|---|---|
| HDL reagent | 60.5 | 60.0 | 1.0 |
| Formulated Reagent D, Formulated Reagent I | 51.2 | 6.8 | 7.5 |
| Formulated Reagent E, Formulated Reagent I | 43.8 | 6.7 | 6.5 |
| Formulated Reagent F, Formulated Reagent I | 40.2 | 6.3 | 6.4 |

The ratios observed with the formulated reagents were higher than the ratio observed with the HDL reagent, and the results indicate that use of phospholipase D in the first step at a lower concentration than in the second step, followed by use of phospholipase D also in the second step, allows more preferential measurement of HDL2 than use of the HDL reagent Example 4

In the same manner as in Example 1, HDL2 and HDL3 were recovered by ultracentrifugation, and Formulated Reagent G or H described below as the first step and Formulated Reagent I as the second step were used in combination to allow the reaction to proceed, to see whether the reaction occurs more specifically to HDL2 than HDL3 by use, in the first step, of sphingomyelinase, and phospholipase D at a lower concentration than in the second step, followed by use of phospholipase D also in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 4. As the HDL reagent, HDL-EX, manufactured by Denka Seiken Co., Ltd., was used in the present Example.

| Formulated Reagent G | | |
|---|---|---|
| BES buffer | 100 mmol/L pH 6.6 | |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Pluronic F68 | 0.25 g/L | |
| Sphingomyelinase | 0.5 U/mL | |
| Phospholipase D (PLDP) | 0.1 U/mL | |

| Formulated Reagent H | | |
|---|---|---|
| BES buffer | 100 mmol/L pH 6.6 | |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Pluronic F68 | 0.25 g/L | |
| Sphingomyelinase | 0.5 U/mL | |
| Phospholipase D (PLDP) | 0.3 U/mL | |

| Formulated Reagent I | | |
|---|---|---|
| BES buffer | 100 mmol/L pH 7.0 | |
| Sodium azide | 0.1% | |
| 4-Aminoantipyrine | 4.0 mmol/L | |
| Peroxidase | 2.4 U/mL | |
| Phospholipase D (PLDP) | 1.0 U/mL | |

TABLE 4

| Sample | Absorbance (mAbs) HDL2 | Absorbance (mAbs) HDL3 | Ratio HDL2/HDL3 |
|---|---|---|---|
| HDL reagent | 60.5 | 60.0 | 1.0 |
| Formulated Reagent G, Formulated Reagent I | 51.6 | 7.6 | 6.8 |
| Formulated Reagent H, Formulated Reagent I | 26.4 | 7.3 | 3.6 |

The ratios observed with the formulated reagents were higher than the ratio observed with the HDL reagent, and the results indicate that use, in the first step, of sphingomyelinase, and phospholipase D at a lower concentration than in the second step, followed by use of phospholipase D also in the second step, allows more preferential measurement of HDL2 than use of the HDL reagent.

Example 5

In the same manner as in Example 1, the HDL2 and HDL3 fractions were recovered by ultracentrifugation, and Formulated Reagent B described below as the first step and Formulated Reagent J or K described below as the second step were used in combination to allow the reaction to proceed, to see whether the reaction occurs more specifically to HDL2 than HDL3 by use of sphingomyelinase in the first step, followed by use of phospholipase C in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 5. As the HDL reagent, HDL-EX, manufactured by Denka Seiken Co., Ltd., was used in the present Example.

| Formulated Reagent B | | |
|---|---|---|
| BES buffer | 100 mmol/L pH 6.6 | |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |

-continued

| | | |
|---|---|---|
| Pluronic F68 | 0.25 g/L | |
| Sphingomyelinase | 0.5 U/mL | |

Formulated Reagent J

| | | |
|---|---|---|
| BES buffer | 100 mmol/L | pH 7.0 |
| Sodium azide | 0.1% | |
| 4-Aminoantipyrine | 4.0 mmol/L | |
| Peroxidase | 2.4 U/mL | |
| Phospholipase C | 1.0 U/mL | |

Formulated Reagent K

| | | |
|---|---|---|
| BES buffer | 100 mmol/L | pH 7.0 |
| Sodium azide | 0.1% | |
| 4-Aminoantipyrine | 4.0 mmol/L | |
| Peroxidase | 2.4 U/mL | |
| Phospholipase C | 2.0 U/mL | |

TABLE 5

| Sample | Absorbance (mAbs) HDL2 | Absorbance (mAbs) HDL3 | Ratio HDL2/HDL3 |
|---|---|---|---|
| HDL reagent | 73.6 | 71.2 | 1.0 |
| Reagent composition B, Reagent composition J | 73.5 | 16.0 | 4.6 |
| Reagent composition B, Reagent composition K | 75.9 | 27.7 | 2.7 |

The ratios observed with the formulated reagents were higher than the ratio observed with the HDL reagent, and the results indicate that use of sphingomyelinase in the first step, followed by use of phospholipase C in the second step allows more preferential measurement of HDL2 than use of the HDL reagent.

Example 6

In the same manner as in Example 1, the HDL2 and HDL3 fractions were recovered by ultracentrifugation, and Formulated Reagent B as the first step and Formulated Reagent L or M described below as the second step were used in combination to allow the reaction to proceed, to see whether the reaction occurs more specifically to HDL2 than HDL3 by use of phospholipase C or D in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 6. As the HDL reagent, HDL-EX, manufactured by Denka Seiken Co., Ltd., was used in the present Example.

Formulated Reagent L

| | | |
|---|---|---|
| BES buffer | 100 mmol/L | pH 7.0 |
| Sodium azide | 0.1% | |
| 4-Aminoantipyrine | 4.0 mmol/L | |
| Peroxidase | 2.4 U/mL | |
| Phospholipase D (PLDP) | 2.0 U/mL | |

Formulated Reagent M

| | | |
|---|---|---|
| BES buffer | 100 mmol/L | pH 7.0 |
| Sodium azide | 0.1% | |
| 4-Aminoantipyrine | 4.0 mmol/L | |
| Peroxidase | 2.4 U/mL | |
| Pluronic F68 | 0.25 g/L | |
| Phospholipase C | 1.0 U/mL | |

TABLE 6

| Sample | Absorbance (mAbs) HDL2 | Absorbance (mAbs) HDL3 | Ratio HDL2/HDL3 |
|---|---|---|---|
| HDL reagent | 73.6 | 71.2 | 1.0 |
| Reagent composition B, Reagent composition L | 69.5 | 12.6 | 5.5 |
| Reagent composition B, Reagent composition M | 69.6 | 12.6 | 5.5 |

The ratios observed with the formulated reagents were higher than the ratio observed with the HDL reagent, and the results indicate that use of phospholipase C or D in the second step allows more preferential measurement of HDL2 than use of the HDL reagent.

Example 7

In the same manner as in Example 1, the HDL2 and HDL3 fractions were recovered by ultracentrifugation, and Formulated Reagent N described below as the first step and Formulated Reagent J or K as the second step were used in combination to allow the reaction to proceed, to see whether the reaction occurs more specifically to HDL2 than HDL3 by use of phospholipase C in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 7. As the HDL reagent, HDL-EX, manufactured by Denka Seiken Co., Ltd., was used in the present Example.

Formulated Reagent N

| | | |
|---|---|---|
| BES buffer | 100 mmol/L | pH 6.6 |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |

TABLE 7

| Sample | Absorbance (mAbs) HDL2 | Absorbance (mAbs) HDL3 | Ratio HDL2/HDL3 |
|---|---|---|---|
| HDL reagent | 138.8 | 54.0 | 2.6 |
| Formulated Reagent N, Formulated Reagent J | 91.7 | 10.1 | 9.1 |
| Formulated Reagent N, Formulated Reagent K | 98.4 | 17.9 | 5.5 |

The ratios observed with the formulated reagents were higher than the ratio observed with the HDL reagent, and the results indicate that use of phospholipase C in the second step allows more preferential measurement of HDL2 than use of the HDL reagent.

Example 8

In the same manner as in Example 1, the HDL2 and HDL3 fractions were recovered by ultracentrifugation, and Formulated Reagent N as the first step and Formulated Reagent L or M as the second step were used in combination to allow the reaction to proceed, to see whether the reaction occurs more specifically to HDL2 than HDL3 by use of phospholipase C or D in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 8. As the HDL reagent, HDL-EX, manufactured by Denka Seiken Co., Ltd., was used in the present Example.

TABLE 8

| Sample | Absorbance (mAbs) | | Ratio HDL2/ HDL3 |
|---|---|---|---|
| | HDL2 | HDL3 | |
| HDL reagent | 138.8 | 54.0 | 2.6 |
| Formulated Reagent N, Formulated Reagent L | 35.0 | 5.4 | 6.5 |
| Formulated Reagent N, Formulated Reagent M | 40.0 | 5.6 | 7.1 |

The ratios observed with the formulated reagents were higher than the ratio observed with the HDL reagent, and the results indicate that use of phospholipase C or D in the second step allows more preferential measurement of HDL2 than use of the HDL reagent.

Example 9

The HDL2 and HDL3 fractions were recovered by ultracentrifugation, and Formulated Reagent V described below as the first step and Formulated Reagent J or K as the second step were used in combination to allow the reaction to proceed, to see whether the reaction occurs more specifically to HDL2 than HDL3 by use of lipoprotein lipase in the first step, followed by use of phospholipase C in the second step. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 9. As the HDL reagent, HDL-EX, manufactured by Denka Seiken Co., Ltd., was used in the present Example.

| Formulated Reagent V | | |
|---|---|---|
| BES buffer | 100 mmol/L | pH 6.6 |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Lipoprotein lipase (LPL-311) | 0.1 U/mL | |

TABLE 9

| | | Absorbance (mAbs) | | Ratio HDL2/ HDL3 |
|---|---|---|---|---|
| | | HDL2 | HDL3 | |
| HDL reagent | | 228.9 | 68.8 | 3.3 |
| Formulated Reagent V | Formulated Reagent J | 63.6 | 10.6 | 6.0 |
| Formulated Reagent V | Formulated K Reagent | 75.0 | 13.1 | 5.7 |

The ratios observed with the formulated reagents were higher than the ratio observed with the HDL reagent, and the results indicate that use of lipoprotein lipase in the first step, followed by use of phospholipase C in the second step allows more preferential measurement of HDL2 than use of the HDL reagent.

Example 10

In the same manner as in Example 1, the HDL2 and HDL3 fractions were recovered by ultracentrifugation, and Formulated Reagent W described below as the first step and Formulated Reagent I or L as the second step were used in combination to allow the reaction to proceed. By this, whether the reaction occurs more specifically to HDL2 than HDL3 by use of lipoprotein lipase in the first step, followed by use of phospholipase D in the second step was observed. After obtaining the results, the absorbance for HDL2 was divided by the absorbance for HDL3 to calculate the ratio of reactivity between HDL2 and HDL3, and the obtained ratio was compared to that in a case where an HDL reagent was used in the test. The results are shown in Table 10. As the HDL reagent, HDL-EX, manufactured by Denka Seiken Co., Ltd., was used in the present Example.

| Formulated Reagent W | | |
|---|---|---|
| BES buffer | 100 mmol/L | pH 6.6 |
| HDAOS | 0.7 mmol/L | |
| Catalase | 600 U/mL | |
| Sodium chloride | 1 g/L | |
| Cholesterol esterase | 1.4 U/mL | |
| Cholesterol oxidase | 0.8 U/mL | |
| Sphingomyelinase | 0.5 U/mL | |
| Lipoprotein lipase (LPL-311) | 0.1 U/mL | |

TABLE 10

| | | Absorbance (mAbs) | | Ratio HDL2/ HDL3 |
|---|---|---|---|---|
| | | HDL2 | HDL3 | |
| HDL reagent | | 228.9 | 68.8 | 3.3 |
| Formulated Reagent W | Formulated Reagent I | 75.0 | 11.5 | 6.5 |
| | Formulated Reagent L | 62.8 | 13.7 | 4.6 |

The ratios observed with the formulated reagents were higher than the ratio observed with the HDL reagent, and the results indicate that use of lipoprotein lipase in the first step, followed by use of phospholipase C or D in the second step allows more preferential measurement of HDL2 than use of the HDL reagent.

Example 11

The CM/VLDL fraction and the LDL fraction were recovered by ultracentrifugation, and Formulated Reagent B as the first step and Formulated Reagent J, K, I or L as the second step were used in combination to allow the reaction to proceed, to confirm that, by use of sphingomyelinase in the first step, followed by use of phospholipase in the second step, lipoproteins other than HDLs are eliminated in the first step and that the reaction is not influenced by such lipoproteins. The influence of lipoproteins other than HDLs on the measurement was studied by calculating the relative ratio based on comparison with the influence observed with an HDL reagent that generally has only small influence on lipoproteins other than HDLs. The results are shown in Table 11. As the HDL reagent, HDL-EX, manufactured by Denka Seiken Co., Ltd., was used in the present Example.

Relative ratio=absorbance obtained with the reagents tested/absorbance obtained with the HDL reagent×100

TABLE 11

| | CM/VLDL fraction | | LDL fraction | |
|---|---|---|---|---|
| | Absorbance (mAbs) | Relative ratio | Absorbance (mAbs) | Relative ratio |
| HDL reagent | 2.9 | | 16.8 | |
| Formulated Reagent B Formulated Reagent J | 2.4 | 82.8% | 17.2 | 102.4% |
| Formulated Reagent B Formulated Reagent K | 2.5 | 86.2% | 17.1 | 101.8% |
| Formulated Reagent B Formulated Reagent I | 2.4 | 82.8% | 14.2 | 84.5% |
| Formulated Reagent B Formulated Reagent L | 2.0 | 69.0% | 14.3 | 85.1% |

In terms of the CM/VLDL fraction and the LDL fraction, the formulated reagents showed almost the same or lower values as compared to the values observed with the general HDL reagent, indicating that lipoproteins other than HDL did not influence the measurement.

The invention claimed is:

1. A kit for quantifying cholesterol in high-density lipoprotein 2, said kit comprising:
   a reagent (i); and
   a reagent (ii),
   wherein the reagent (i) comprises cholesterol esterase, cholesterol oxidase, N-(2-hydroxy-3-sulfopropyl)-3,5-dimethoxyaniline (HDAOS), a catalase, a monovalent or divalent cation(s) or a salt(s) thereof and an polyoxyethylene-polyoxypropylene condensate, and the reagent (i) does not include a phospholipase C, a phospholipase D, sphingomyelinase and 4-aminoantipyrine,
   wherein the reagent (ii) comprises a phospholipase D, 4-aminoantipyrine, peroxidase and an effective catalase inhibiting amount of sodium azide, and wherein the reagent (ii) does not include cholesterol esterase and cholesterol oxidase.

2. The kit according to claim 1, wherein the concentration of said phospholipase D in the reagent (ii) is 0.1 to 200 U/mL.

3. The kit according to claim 2, wherein the concentration of said phospholipase D in the reagent (ii) is 1.0 to 50 U/mL.

4. The kit according to claim 1, wherein said polyoxyethylene-polyoxypropylene condensate is Pluronic P123.

5. The kit according to claim 1, wherein the concentration of said polyoxyethylene-polyoxypropylene in the reagent (ii) is 0.002 to 3.0% by weight.

6. The kit according to claim 1, wherein the monovalent and/or divalent cation(s) and/or the salt(s) is sodium chloride.

7. The kit according to claim 6, wherein the concentration of said sodium chloride is 5 to 30 g/L.

8. The kit according to claim 1, wherein the concentration of said catalase is 600 U/mL.

9. The kit according to claim 1, wherein the concentration of said cholesterol esterase is 0.2 to 2.0 U/mL.

10. The kit according to claim 1, wherein the concentration of said cholesterol oxidase is 0.1 to 1.0 U/mL.

11. The kit according to claim 1, wherein the concentration of said N-(2-hydroxy-3-sulfopropyl)-3,5-dimethoxyaniline is 0.5 to 2.0 mmol/L.

12. The kit according to claim 1, wherein the concentration of said sodium azide is 0.1 g/L to 1.0 g/L.

13. The kit according to claim 1, wherein the concentration of said 4-aminoantipyrine is 0.1 to 2.0 mmol/L.

* * * * *